United States Patent
Skewes et al.

(10) Patent No.: US 6,206,863 B1
(45) Date of Patent: Mar. 27, 2001

(54) METHOD AND SYSTEM FOR CLEANSING THE SKIN

(75) Inventors: Susan Skewes, New London, CT (US); Russell E. Raddatz, Cayce, SC (US)

(73) Assignee: Incline Technologies, Inc., Reno, NV (US)

(*) Notice: Subject to any disclaimer, the term of this patent is extended or adjusted under 35 U.S.C. 154(b) by 0 days.

(21) Appl. No.: 09/221,808

(22) Filed: Dec. 29, 1998

Related U.S. Application Data (63) Continuation of application No. 08/618,732, filed on Mar. 20, 1996, which is a continuation of application No. 08/266,963, filed on Jun. 27, 1994, which is a continuation-in-part of application No. 08/203,230, filed on Feb. 28, 1994, now abandoned.

(51) Int. Cl.[7] ............ A61M 38/00; A61K 35/00; A01N 25/34
(52) U.S. Cl. ............ 604/290; 602/289; 424/123; 424/404
(58) Field of Search ............ 602/41–59; 206/440, 206/441, 223, 205, 209, 210, 229, 361, 494, 37, 812, 824, 823, 828; 128/888, 889; 15/27, 167.1; 132/317; 604/289, 290, 292, 293; 442/123, 153, 165, 402, 405; 428/36.2

(56) References Cited

U.S. PATENT DOCUMENTS

| | | |
|---|---|---|
| 1,507,707 | 9/1924 | Morganstern . |
| 1,619,180 | 3/1927 | Benussi . |
| 3,404,010 | 10/1968 | Wilds . |
| 3,608,708 | 9/1971 | Stornadt . |
| 3,638,789 | 2/1972 | Tuszewski . |
| 3,965,519 | 6/1976 | Hermann . |
| 4,065,826 | 1/1978 | Hough . |

(List continued on next page.)

FOREIGN PATENT DOCUMENTS

| | | |
|---|---|---|
| 331573 | 3/1985 | (DE) . |
| 032793 | 7/1981 | (EP) . |
| 2647091 | 11/1990 | (FR) . |
| 2163947 | 3/1986 | (GB) . |
| 2190289 | 11/1987 | (GB) . |
| 2211093 | 6/1989 | (GB) . |
| 2218430 | 11/1989 | (GB) . |
| 63-160658 | 4/1988 | (JP) . |

OTHER PUBLICATIONS

Skewes, Susan M., "No More Bed Baths!", RN Magazine, Jan. 1994, pp. 34–35.

Skewes, Susan M., RN, ONC, "The Bag Bath—A Theory Based Alternative To the Traditional Bed Bath", Aug. 1992.

*Primary Examiner*—Kim M. Lewis
(74) *Attorney, Agent, or Firm*—Christie, Parker & Hale, LLP (57) ABSTRACT

A kit containing a plurality of sheets impregnated with a hydrating, non-ionic cleanser in a microwave-heatable container for use in bathing a patient or for personal bathing. In one embodiment, the sheets are preferably 9"×9" in dimension, and made of a non-woven cotton or polyester/cotton blend. Alternatively, the sheets can be made in the form of mittens by joining the material so that one side remains open for the insertion of the hand of the user, and have an outer, absorbent layer and an inner, moisture-proof layer. The cleanser preferably is a mixture of de-ionized water, at least one non-ionic surfactant, a humectant and/or a hydrating emollient, and vitamin E that is intended to remain on the skin rather than be rinsed. The solution may also contain a preservative such as biguanide or be sterilized. In use, the kit is heated and then each sheet or mitten is applied to a separate portion of the body, to limit the risk of cross contamination. The used sheets and mittens are discarded in a waste receptacle thus avoiding reuse of contaminated bathing equipment and thereby reducing the incidence of nosocomial infection. The cleanser evaporates quickly in air, leaving the skin clean, soft, soothed, nourished and protected.

26 Claims, 4 Drawing Sheets

U.S. PATENT DOCUMENTS

| | | | |
|---|---|---|---|
| 4,090,844 | 5/1978 | Rowland . | |
| 4,091,491 | 5/1978 | Hoffman . | |
| 4,112,167 | 9/1978 | Dake et al. | 428/154 |
| 4,343,403 | 8/1982 | Daniels et al. | 206/812 |
| 4,347,931 | 9/1982 | Ginger et al. | 206/438 |
| 4,523,348 | 6/1985 | Petrie | 15/227 |
| 4,615,937 | 10/1986 | Bouchette | 428/288 |
| 4,725,489 | 2/1988 | Jones et al. | 428/289 |
| 4,749,080 | 6/1988 | Toohey | 206/210 |
| 4,781,974 | 11/1988 | Bouchette et al. | 428/288 |
| 4,788,733 | 12/1988 | Lerner | 15/104.94 |
| 4,810,567 | 3/1989 | Calcaterra et al. | 428/224 |
| 4,837,079 | 6/1989 | Quantrill et al. | 428/288 |
| 4,847,071 | 7/1989 | Bissett et al. | 424/59 |
| 4,877,816 | 10/1989 | Murabayashi et al. | 521/92 |
| 4,902,283 | 2/1990 | Rojko et al. | 604/290 |
| 4,948,585 | 8/1990 | Schlein | 424/404 |
| 4,959,881 | 10/1990 | Murray | 15/227 |
| 4,964,188 | 10/1990 | Olson | 15/227 |
| 5,019,058 | 5/1991 | Storandt | 604/290 |
| 5,050,737 | 9/1991 | Joslyn et al. | 206/494 |
| 5,229,105 | 7/1993 | Wilmsmann | 424/59 |
| 5,229,963 | 7/1993 | Wilmsmann | 424/59 |
| 5,256,417 | 10/1993 | Koltisko | 424/402 |

FIG. 4

METHOD AND SYSTEM FOR CLEANSING THE SKIN

This application is a continuation of U.S. application Ser. No. 08/618,732, filed Mar. 20, 1996, now abandoned, which is a continuation of U.S. application Ser. No. 08/266,963, filed Jun. 27, 1994, now abandoned, which is a continuation-in-part of application Ser. No. 08/203,230, filed Feb. 28, 1994, now abandoned.

BACKGROUND OF THE INVENTION

1. Field of the Invention

The present invention relates generally to cleansing the skin. More particularly, the present invention relates to a method and system for bathing a patient in a hospital, a nursing home or for personal bathing.

2. Discussion of Background

The skin is the largest organ of the human body. As a boundary layer, it has two functions: containing other organs of the body and acting as a barrier. Its effectiveness as a barrier depends on its physical integrity. Preserving that integrity is an important part of maintaining good health. However, when skin is dry, it tends to itch, flake and crack; skin dryness leads to a higher incidence of pruritis and hastens the formation of pressure ulcers, a concern for all patients but an especial concern to elderly and orthopedic patients. In the United States, pressure ulcers cost between $10 billion and $15 billion to treat each year, an average of $45,000 each. The in-hospital death rates for patients with pressure ulcers has been estimated to be as high as 23%. Accordingly, the United States Department of Health and Human Services, Public Health Service, Agency for Health Care Policy & Research, published guidelines in 1992 consistent with the recommendations of the National Pressure Ulcer Advirsory Panel that are directed to care of patients in hospitals (Clinical Practice Guideline No. 3, Pressure Ulcers in Adults: Prediction and Prevention). The guidelines specify avoiding hot water, low humidity, irritating and drying of the skin and encourages the use of mild cleansers in bathing patients.

Dryness of skin can result from a number of factors, including aging, exposure to wind, heat, air conditioning, and washing with soap. Because the skin of the elderly has less subcutaneous fat, the aging process has been associated with a decrease in the ability of the lipids in skin to bind water. It has been estimated that 59% to 75% of the elderly have some decree of skin impairment upon admission to hospitals.

Washing with soap is a particular concern for skin condition and health in hospitals. The traditional bath given to patients involves the use of wash cloths, soap and a plastic basin. The basin is filled with warm water and taken to the patient's bedside. The patient is bathed by applying soap to a cloth, rubbing the cloth over the patient's skin, and rinsing the skin with water. The patient's skin is then dried using a towel. The textbook approach recommends frequent changes of the water and the wash cloths.

In practice, because of time contraints, the textbook approach is seldom observed. Use of the same water and cloth for bathing the entire body results in areas of the patient's body becoming contaminated by bacterial flora carried from other parts. Bars of soap and basins (often stored with bedpans in a warm, dark cabinet between use with the same or a different patient) culture gram-negative bacteria which are pathogenic and can cause impairment and infection of skin tissues. Studies have shown that a patient is usually microbiologically more contaminated after the bath than before.

Another problem with the traditional bathing approach is friction against the skin. Friction from the use of wash cloths and towels damages skin tissue. Furthermore, to reduce the cost of linens—a major cost factor in hospital budgets—, towels and wash cloths of inferior quality are purchased for patient bathing and they are used longer before being discarded. Consequently, the texture of towels and wash cloths for bathing patients is coarser, further exacerbating the condition of their skin.

Furthermore, the traditional bathing procedure is both time-consuming, requiring 30–45 minutes per patient per day, and has a relatively high direct cost because of the time involved.

Washing with soap also has a high indirect cost. There is a protective coating on the skin formed from sebum secreted by the hair follicles and dead skin cells. This coating, or "acid mantle," has bacteriostatic and fungistatic properties. Soap impairs the skin in two ways. First, soap immulsifies skin lipids which hold moisture, leaving the skin drier; and, second, soap, being alkaline, destroys the acid mantel of the skin. Washing with soap is therefore a major physiological risk to the individual, because bacteria can survive longer on the soap-washed skin and can gain entrance to the interior skin layers and the blood stream through dried, cracked skin or pressure ulcers.

In the January 1994 issue of RN Magazine, a procedure was reported for bathing patients that is not based on this traditional procedure. The new procedure involves use of a set of wash cloths soaked in a dilute solution of a cleanser composed substantially of mild soap and water. This cleanser does not need to be rinsed; it evaporates quickly from the skin. The cloths are placed in a plastic bag, heated in a microwave oven until warm, and then applied to defined areas of a patient's body, one cloth per area. The cloths are laundered between uses. There is no basin. The cleanser is not rinsed, but dries quickly without toweling. Only the areas with large skin folds are gently patted dry. An extensive study of this procedure compared to the traditional one showed that the patient's felt cleaner, skin condition was better and the costs were reduced by a factor of four, largely because of less time being needed to bathe a patient. Skin integrity improved statistically by 56% from admission to discharge from the hospital. However, the time taken to bathe a patient was partially offset by the labor involved in preparing the cloths. Furthermore, the cloths cannot be prepared far in advance because of the limited storage space and, more importantly, the inevitable growth of bacteria associated with this procedure.

There have been other attempts to develop a product for bathing a patient or cleansing skin. For example, Storandt (U.S. Pat. No. 5,019,058) teaches an applicator mitt for a variety of uses including applying ointment for treating injured parts of the body. Storandt's mitt is in the form of a pouch within a heat sealed package. The material is two-ply, including a non-woven fabric and a thermoplastic film such as polyethylene or EVA.

Two mittens have been developed for use in chancing the diapers of babies and in performing the associated cleansing. The more recent of these is by Rojko, et al. (U.S. Pat. No. 4,902,283) and is a simple cylindrical mitt for cleaning babies, with an outer layer of cotton and a water-repellent inner layer. The cotton layer is stitched and the inner layer can be made of polypropylene. Rojko, et al. also teach the rotation of the mitt by 180° to use "the other side."

The other baby mitten is disclosed by Lerner in U.S. Pat. No. 4,788,733. He teaches a two-ply glove for cleaning babies. Lerner also teaches impregnating his mitten with a cleaning solution.

In U.S. Pat. No. 4,523,348, Petrie describes a so-called nurse's mitt expressly for bathing a patient. This mitt is broadcloth-backed terry cloth and has features designed for convenience in gripping the mitt.

Ginger, et al. (U.S. Pat. No. 4,347,931) also provide a mitt for cleaning a patient as well as applying an antiseptic. Their mitt is rectangular and two-ply, with a plastic, non-porous inner layer and an absorbent outer layer. The mitt, which is described as disposable, is impregnated with a cleaning solution and placed in an outer package that is opened just prior to use.

However, there remains a need for a system for bathing that is effective for skin cleansing, practical, inexpensive and minimizes damage to the protective acid mantle of the skin.

SUMMARY OF THE INVENTION

According to its major aspects and broadly stated, the present invention is a method system comprising a prepared "kit" for skin cleansing. Use of the kit does not damage the acid mantle but is believed to soothe, nourish and protect the skin. The kit includes a sealable container that can be heated, preferably in a microwave oven, and a plurality of sheets impregnated with a substantially non-ionic, hydrating cleanser. Preferably, the sheets are made of a non-woven cotton or blend of polyester and cotton. The size of each sheet should be large enough to cover the size of an average outstretched hand. Normally, a 9"×9" sheet is of sufficient size, however, the sheet can be larger if desired. Alternatively, the sheets can be made in the form of "mittens" if desired. In this embodiment, a set of mittens is impregnated with the substantially non-ionic, hydrating cleanser. The mittens are formed from rectangular, two-ply sheets heat sealed so that the user's hand can be inserted inside the mitten from the open end. Each mitten has an absorbent layer of polyester cotton adhered to a moisture-impervious layer, with the moisture-impervious layer on the inside and the absorbent layer on the outside of the mitten. The cleanser is preferably a mixture that includes at least one non-ionic surfactant, vitamin E, a humectant and/or an emollient such as dexpanthenol and de-ionized water. The sheets or mittens in the container are sterilized, or, optionally, a di-acid base such as biguanide can be added as a preservative to increase shelf life. This cleanser is moisturizing, non-rinsing, and fast drying.

Use of the present invention would significantly lessen the incidence of pressure ulcers. Perhaps more importantly, its use is believed to be essential in certain types of cases of especially high risk for infection, such as bone marrow transplant victims, burn victims, and other cases where in the auto-immune system of an individual is suppressed, such as AIDS patients.

An important feature of the present invention is the combination of a plurality of pre-impregnated sheets and the container. The exact number depends on use, as will be described in more detail in the Detailed Description of Preferred Embodiments. This combination of sheets and container provides a single-use, yet complete, sterilizable, compact personal bathing kit that can be made to high quality standards well in advance of need. The kit may be heated slightly for comfort, and the sheets can then be used to cleanse the eight zones of a human body. Each sheet can clean one zone of the body; if in "mitten" form, there is one clean mitten per zone. One kit bathes one patient, and each kit is discarded after use. Thus, the kits lend themselves to a manufacturing process that will minimize the labor involved in kit assembly and assures kit cleanliness, sterility, uniformity, and accurate formulation of the cleansing mixture. The system of the present invention complies with the National Pressure Ulcer Advisory Panel recommendations, avoids cross contamination of the patient and reduces the incidence of nosocomial infections. Furthermore, the manufacturing of a single use "kit" assures that the quality of the kit is uniformly high and that the kits are compact to minimize space storage requirements.

The non-woven cotton or blend of cotton/polyester for the material of the sheets is another feature of the present invention. The sheets are durable and can remove dirt, yet are soft, and do not chemically react with either the impregnated solution or the patient's body. The non-woven sheets are chemically stable to microwaves and are heat retentive. Moreover, the sheets, which can be manufactured in any convenient shape, are absorbent, assuring the retention of enough solution for effective cleansing, and soft and smoothe for low friction. Finally, these sheets are simple and inexpensive to manufacture, making them more affordable as a disposable item than traditional, woven cotton wash cloths and more effective than paper products.

Another important feature of the present invention is the cleanser itself. By being substantially non-ionic, as a result of the use of non-ionic surfactants and de-ionized water, it cleanses without disturbing the acid mantle of the skin or leaving behind minerals and chlorine. Damage to this layer and its bacteriostatic and fungistatic properties is thereby avoided. Preservation of the acid mantle is especially important in a hospital environment where bacteria abound and the patient's resistance to nosocomial infection may be less than that of a healthy individual. De-ionized water does not have ions present in the same concentrations that are present in tap water. The additional ingredients are believed to soften, soothe, nourish and protect the skin.

Still another feature of the present invention is the method of impregnating the sheets during the manufacturing process. The sheets are first saturated with cleansing solution, then the excess is removed by squeezing the sheets with sufficient pressure so that just the excess is removed. This method assures the even distribution of the solution in just sufficient quantity for the task of cleansing. Removing excess solution also reduces weight and bulk of the kit, making it easier and less expensive to transport and store large numbers of kits.

Being able to sterilize the kit at a manufacturing facility is another feature of the present invention. Sterilization is achieved by subjecting the kit to ultraviolet light, electron beam, or gamma radiation. Sterilization extends the shelf life indefinitely and allows use of the kits following emergencies, natural disasters, military action, and hospital emergencies involving loss of water. The present invention can also be used in locations where clean water is not readily available such as by those who live in remote areas, by campers, and by those on boats.

The sealable, moisture-proof, microwave-transparent container is another feature of the present invention because it enables the mittens to be impregnated in advance without concern that they might dry out or lose effectiveness, either during storage or during warming. Additionally, the container is sterilizable using a number of sterilization techniques and does not react or degrade upon contact with the sheets or the impregnated solution.

The configuration of the mittens, contained in one embodiment, is another feature of the present invention. The mittens can be made of two-ply sheets, heat sealed, and then cut.

Still another feature of the present invention is the moisture-impermeable layer on the inside of each mitten. This layer provides the user added protection from prolonged exposure to moisture as well as bacteria and viruses from the patient, such as the virus that causes AIDS and hepatitis.

Finally, another feature of the present invention is that, in the preferred embodiment, it is made of disposable and recyclable materials.

Other features will be recognized for their advantages by those skilled in the art through carefully reading the Detailed Description of the Preferred Embodiment accompanied by the following drawings.

BRIEF DESCRIPTION OF THE DRAWINGS

In the figures.

DETAILED DESCRIPTION OF PREFERRED EMBODIMENTS

As used herein, a "system" or "kit" is a group of related items that, when brought together, cooperate to achieve a function. Here, the system includes a container, a set of sheets, preferably as flat sheets or formed into mittens that are impregnated with a cleanser. Before use, the system is in a "kit" form where the mittens are in the container and are impregnated with the cleanser. During use, one or more mittens are removed one at a time from the container, used to cleanse skin, and then discarded.

The number of sheets or mittens depends on the use. In its primary configuration, there are eight sheets or mittens for the eight zones of the body. A smaller kit, containing four sheets or mittens, is preferred for partial bathing or episodes of incontinence. A still smaller kit of two sheets or mittens is preferred for small children and cleansing just the face and hands. Finally, for bathing an incontinent patient, a set of ten sheets or mittens is preferred.

Figure 1:
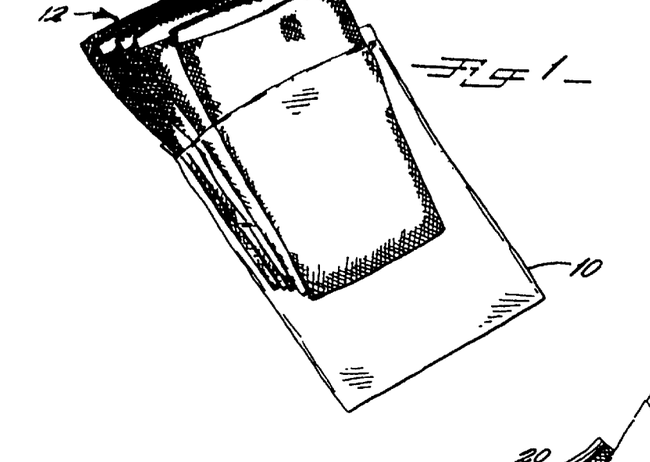
FIG. 1 is a perspective drawing of a system according to a preferred embodiment of the present system.

Referring now to FIG. 1, there is illustrated one embodiment of the present invention comprising a container 10 with a set of "mittens" 12. The term "mitten" refers to a part of the present kit that is used by inserting the hand of the user therein and that does not necessarily have separately defined areas for receiving the individual fingers of the user's inserted hand. Container 10 is preferably a simple, sturdy, sealable, substantially microwave-transparent plastic bag. It is dimensioned to hold the set of mittens 12 and to be heatable in a microwave oven, hot water or hydroculator. Alternatively, container 10 might be a metal foil pouch that can be heated in a conventional oven or hydroculator. A plastic container intended for microwave heating is preferably opened by using notched edge or a perforated tear end (not shown) or other easily-made opening, such as a "rib-and-groove" seal. Container 10 itself is preferably opened by a perforation along one edge that can be opened by tearing along the perforations to unseal container 10.

Each mitten (see FIGS. 2 and 3) can be and preferably is made of a two-layered sheet of material, such as non-woven cotton or a polyester/cotton blend, with a first, absorbent layer 18 adhered to a second, moisture-impervious layer 20 so that the mitten is rectangular (as shown) or semi-oval. These layers may be adhered by flame laminating or heat sealing or other standard technique. The rectangle is formed into mitten 12 by heat sealing two separate sheets or by making a fold 22, moisture-impervious layer 20 inside and leaving one side slightly longer than the other, preferably by one-half inch, and then joining edges 24, 26, on either side of fold 22 by radio-frequency welding, heat-sealing or sewing, leaving one remaining edge 28 unsealed. Mitten 12 should be large enough for a user to fit a hand 32 comfortably inside.

Figure 2:
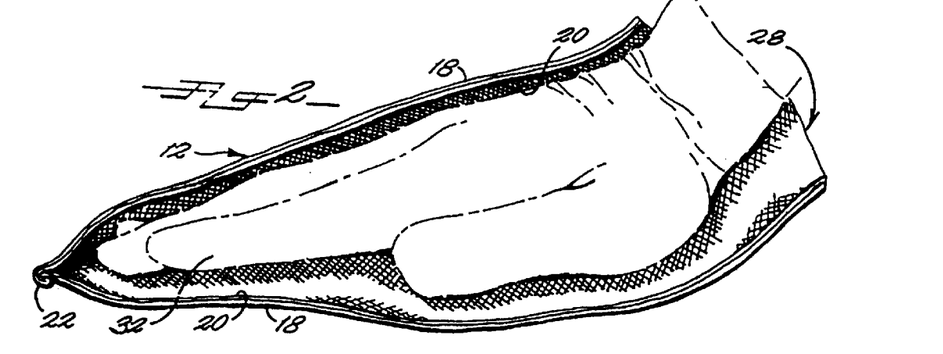
FIG. 2 is a side cross-sectional view of a mitten from the system shown in FIG. 1 with a hand indicated inside the mitten.
Figure 3:
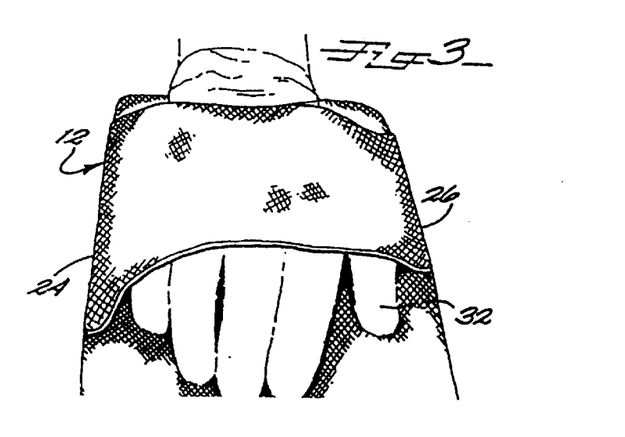
FIG. 3 is an end view, partially cut away, of a mitten from the system shown in FIG. 1 with a hand indicated inside the mitten.

Absorbent layer 18 is made of a material and of enough such material that it will absorb and hold a quantity of cleanser sufficient to cleanse a portion of the body. Materials made of paper, cotton, and synthetic fibers are suitable, but preferably a cotton-polyester blend is used because of its absorbency, heat-retentive qualities, strength and low cost. This blend also has a low coefficient of friction against the human body that will remove dirt but without damaging skin tissue. Moisture-impervious layer 20, which is preferably a synthetic rubber or plastic such as polypropylene or polyethylene, is to help reduce the exposure of the hands of the user to moisture and to bacteria and viruses.

The cleanser is substantially non-ionic and very slightly acidic (pH 6.5–6.7) to preserve the acid mantle. An ionic cleanser, especially a strong base like soap, is harmful to this natural barrier. Preferably, the cleanser includes one or more surfactants (F68 and F108, for example), wetting agents that are non-ionic and that are dissolved in de-ionized water. De-ionized water will have fewer ions (and bacteria) than tap water and will also have a very slightly acidic pH between approximately 6.5 and approximately 6.7. The water alternatively can be purified through reverse osmosis, hyperfiltration or other technique. Also, the cleanser includes a hydrating factor or humectant, commonly called a moisturizer for retaining water, or an emollient for holding in the moisture, or both. Finally, the cleanser includes vitamin E and may also include a di-acid base such as biguanide as a preservative. Such a cleanser is manufactured by Sage Pharmaceutical and sold under the trademark DERMACLIN.

By reducing surface tension, surfactants enable the ingredients of the present solution to mix better with each other and they wet the skin surface better to enable the solution to spread more easily. Unlike cleansers, the preferred surfactant F68, regardless of concentration, does not inhibit the skin's ability to fight infection.

Biguanide is formed by the action of an ammodiacal solution of cupric oxide and dicyanodiamide and is of the form:

2[—NH.C(NH)NH2]

Biguanide is related to guanine, one of the four amino acids that form the genetic code. Biguanide is believed to have anti-bacterial and anti-viral properties and acts as a preservative. Vitamin E has been known to promote the healing of skin for several years. Humectants absorb water molecules; emollients hold moisture to the skin.

The contents of the kit may be sterilized by subjecting the sheets and container to ultraviolet light, electron beam, gamma radiation or other technique. If the kit is to be sterilized, biguanide may not be needed.

This cleansing mixture does not dry the skin, and it does not have to be rinsed. All of the ingredients remaining after evaporation are intended to remain on the skin to seal in moisture, yet without leaving a harmful or uncomfortable residue, hence the term "non-rinsing," which minimizes cross contamination and water exposure; specifically, the term "non-rinsing" is used to mean that the solution should not be rinsed from the body (although it can be), but is intentionally left to dry. While not wishing to be bound by theory, it is believed that the combination in the cleansing solution not only cleanses but protects, soothes, softens and nourishes the skin.

The mittens are designed to be disposable; that is, they are made of cost-effective and biodegradable or recyclable materials and are mass producable so that the cost of the kit is lower than the cost of laundered wash cloths. Therefore, in the present context, disposable means that the mittens are used once and then thrown away in an appropriate receptacle for disposal or recycling, but not laundered for reuse.

Figure 4:
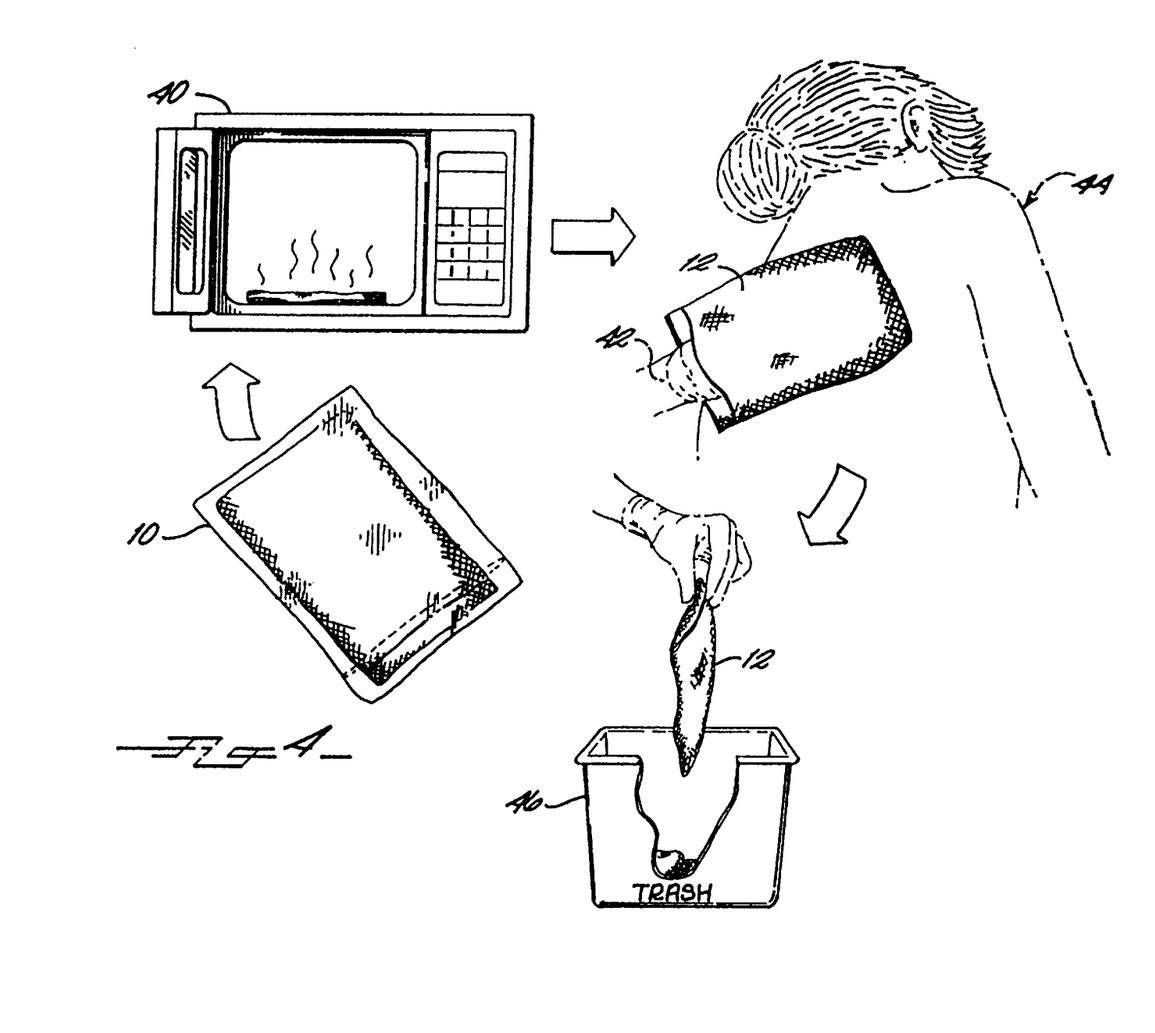
FIG. 4 is a perspective schematic view of a method of using a mitten according to a preferred embodiment of the present invention.

In use, container 10 is unsealed by tearing from a notched edge or along a perforated end, placed in a microwave oven 40 and heated to a selected temperature until warm to the touch, but not hotter than 120° F. or 56° C. (see FIG. 4) and preferably about body temperature. Then container 10 is opened and one mitten 12 removed at a time. The user places a hand 42 inside the first mitten 12 and washes a portion of the body of a patient 44. When that portion has been washed, mitten 12 is discarded into an appropriate waste receptacle 46, and the next mitten withdrawn from container 10. Each mitten is used in sequence and then discarded. This approach prevents the contamination of one part of the body by bacterial flora from another.

Figures 5A, 5B:
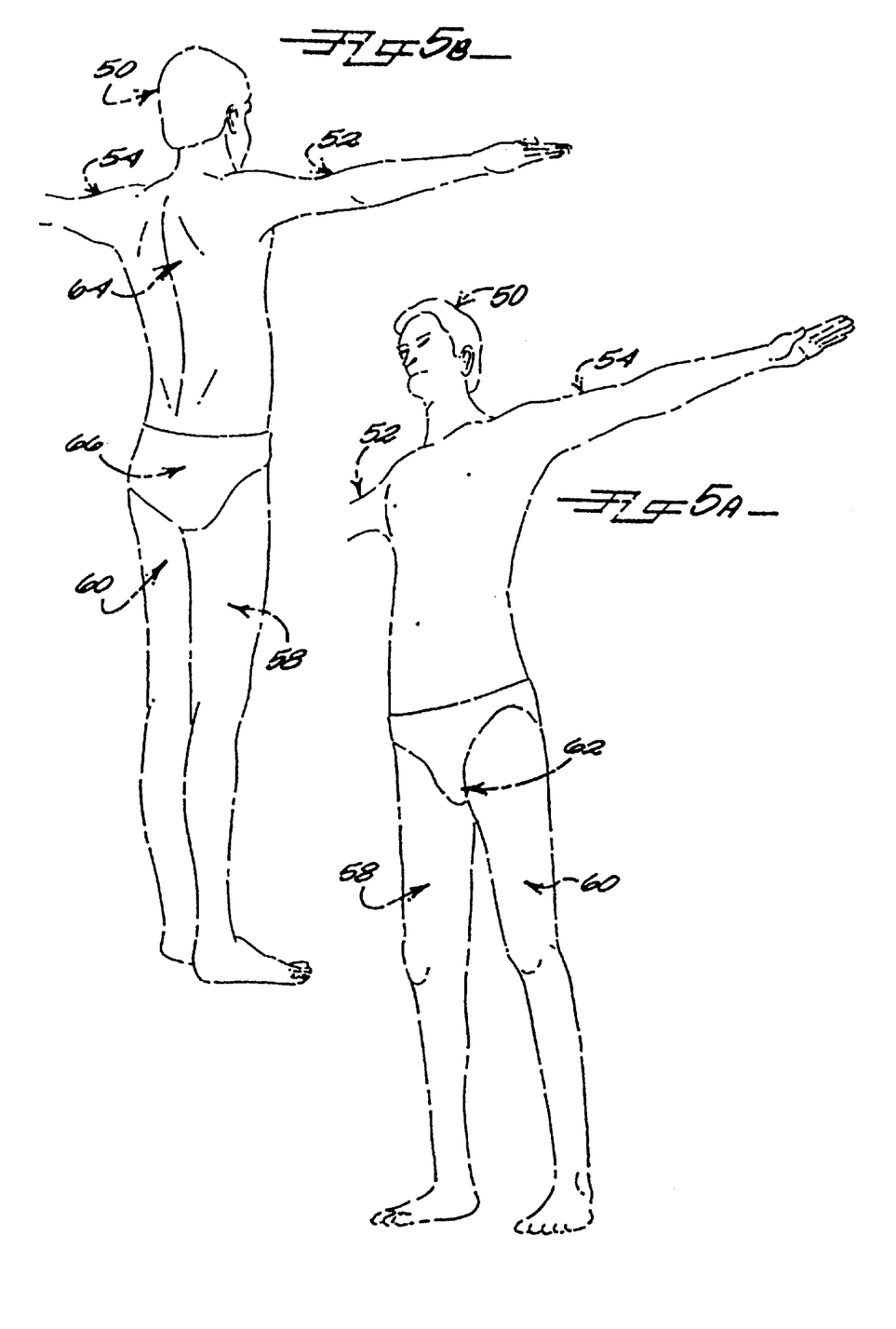
FIGS. 5a and 5b illustrate the nine areas of a human body to be cleansed according to the method and using the system of the present invention.

The areas of the body are illustrated in FIGS. 5a and 5b. These areas include the head, neck and chest area 50, the right arm 52, the left arm 54, the right lea 58, the left leg 60, the perineum 62, the back 64 and the buttocks 66.

Whether in the form of mittens or sheets, the following process is used to bathe the body. The first mitten 12 is used on the patient's face, neck and chest area 50. The first mitten 12 is then discarded and the second mitten 12 withdrawn from container 10. One at a time, second and third mittens 12 are applied to the patient's right arm 52, including its axilla, and to his left arm 54, including the left axilla, respectively. The second and third mittens 12 are discarded as each one is used. The fourth mitten 12 is applied to the patient's right leg 58, discarded, and a fifth mitten 12 applied to his left leg 60, and it, too, is discarded. A sixth mitten 12 is removed and applied to the patient's perineal area 62. Finally, the seventh and eighth mittens 12 are applied to the patient's back 64 and buttocks 66, respectively, each being discarded after use.

Figures 6, 7:
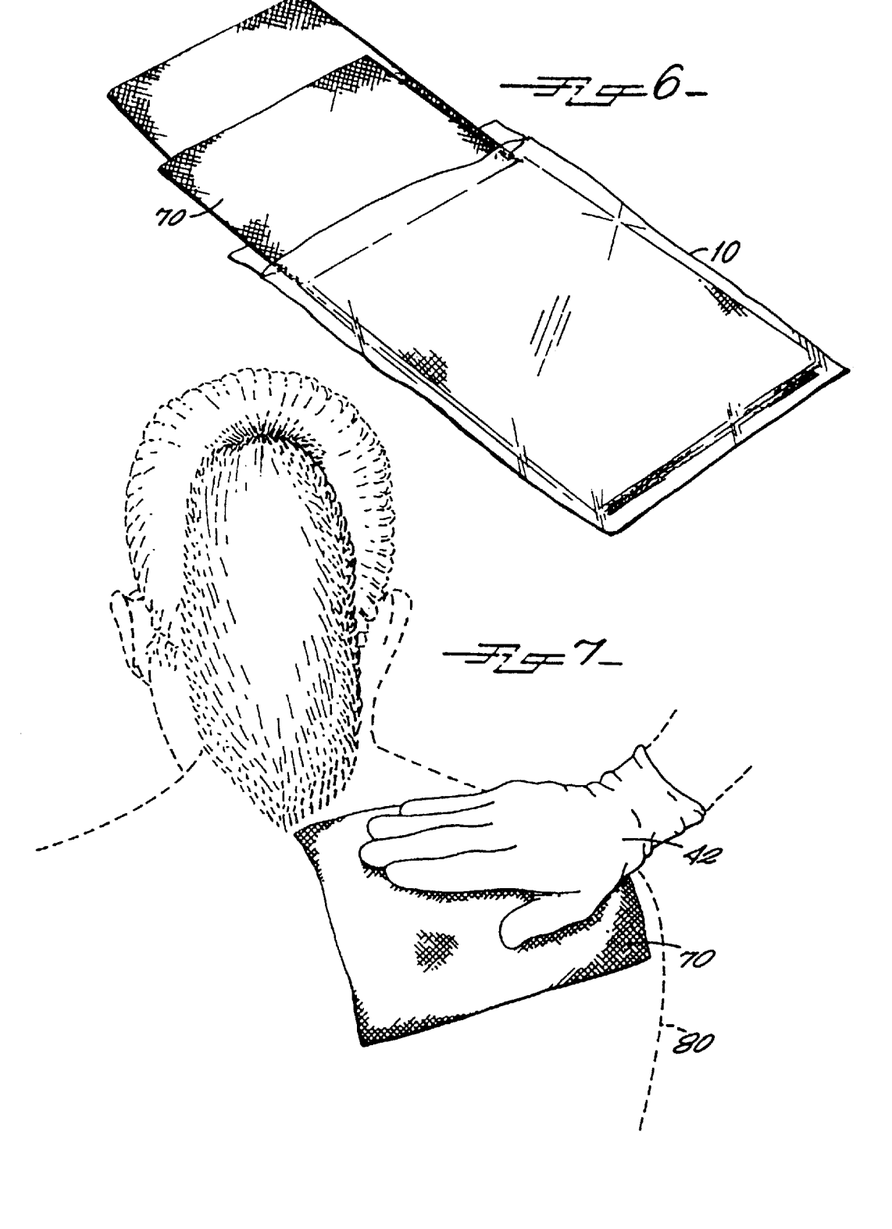
FIG. 6 is a perspective drawing of a system according to an alternative preferred embodiment of the present system.
FIG. 7 is a perspective schematic view of a method of using a sheet according to an alternative preferred embodiment of the present invention.

Referring to FIG. 6, there is illustrated an alternative preferred embodiment of the present invention comprising container 10 and a plurality of sheets 70. Preferably, container 10 is dimensioned to hold between two and twelve sheets 70. Sheets 70 can be made of any chemically stable, non-reactive, heat retentive, absorbent, soft and non-abrasive material. Preferably, sheets 70 are made of a non-woven blend of polyester and cotton, due to the knitted blend's low cost and superior absorbency characteristics. Sheets 70 are impregnated with cleanser, and can be manufactured in any size or shape, but should be large enough to cover an outstretched human hand. Normally, a 9"×9" sheet is of sufficient size.

The cleanser is applied to sheets 70 by first saturating the sheets in the cleanser, and subsequently removing the excess cleanser by "ringing" or squeezing between rollers until a moist, but less than saturated sheet is achieved. This method of impregnation is necessary to ensure a just-sufficient amount of cleanser for effective cleaning without abrasion but no excess runs from the sheet when applied to the skin. Excess solution is both wasteful, can run when applied to the patient and affects evaporation time. Furthermore, removal of excess solution reduces both bulk and weight. By careful packing of moistened sheets in a container, a ten-to-one reduction of bulk can be achieved over the former process using soaked wash clothes. Transportation and storage costs are reduced as is the cost of the solution. These costs are not trivial; it is important, given the number of baths given patients in hospitals, to keep the cost associated with each disposable kit low.

FIG. 7 illustrates an alternative embodiment in use. As with the previous embodiment of the present invention, container 10 is placed in a microwave oven 40 and heated until just warmed to the touch, but not hotter than 120° F. or 56° C. and preferably about body temperature. Then container 10 is opened and one sheet 70 is removed. The user grasps sheet 70 with hand 42 and cleans a portion of the patient's body 80. After use, sheet 70 is discarded and the process repeated until the patient is fully cleansed.

Use of a kit in accordance with the preferred embodiments and method of the present invention avoids cross contamination and the spread of nosocomial infection, reduces the incidence of pressure ulcers and complies with the recommendations of the National Pressure Ulcer Advisory Panel and the AHCPR Guidelines. It provides a solution to the bathing needs of immuno-system suppressed individuals. It provides a portable, light-weight cleansing kit for individuals who have a stoma, such as ostomy, colostomy, and ileostomy, and who presently have a high risk of skin breakdown at the peri-stomal site, to cleanse without using soap, water and a wash cloth. It offers substantial cost savings over the former procedures. Furthermore, a kit accordingly to the present invention can be used for personal bathing, for example, for otherwise healthy individuals who are concerned with the condition of their skin or whose skin is at risk, such as the elderly, or when conventional bathing is not possible or practical, such as during emergencies, natural disasters, on board a sailboat or when camping.

It will be apparent to those skilled in the art from a reading of the foregoing detailed description that many modifications and substitutions may be made in the preferred embodiment described without departing from the spirit and scope of the present invention, which is defined by the appended claims.

What is claimed is:

1. A method for washing two or more selected portions of a body comprising the steps of:
    (a) providing a factory-made sealed package containing a plurality of cloths, each cloth carrying a cleanser;
    (b) heating the package and cloths contained therein to a selected temperature;
    (c) removing a cloth from the package and using the removed cloth to wash only one selected portion of the body;

(d) repeating step (c) until each selected portion of the body has been washed; and (e) disposing of each cloth after use.

2. The method of claim 1, wherein the sealed package consists essentially of a microwave-transparent material.

3. The method of claim 1, wherein the sealed package is disposable.

4. The method of claim 1, wherein the number of selected body portions is at least four and the package contains at least four cloths.

5. The method of claim 1, wherein the number of selected body portions is at least eight and the package contains at least eight cloths.

6. The method according to claim 1 wherein the selected portions of the body include the head, the neck and chest area, the right arm, the left arm, the right leg, the left leg, the perineum, the back and the buttocks.

7. The method of claim 1, wherein each cloth comprises non-woven fibers.

8. The method of claim 1, wherein each cloth comprises synthetic fibers.

9. The method of claim 1, wherein each cloth comprises natural fibers.

10. The method of claim 1, wherein each cloth comprises a blend of natural and synthetic fibers.

11. The method of claim 1, wherein each cloth comprises cotton fibers.

12. The method of claim 1, wherein each cloth has a thickness, weight and moisture content such that the cloth is capable of maintaining its temperature above body temperature until each selected portion of the body has been washed.

13. The method of claim 1, wherein the cleanser comprises a non-ionic surfactant.

14. The method of claim 1, wherein the cleanser has an acidic pH.

15. The method of claim 1, wherein the package is heated by microwaving.

16. The method of claim 1, further comprising sterilizing the cloths in the sealed package.

17. The method of claim 1 wherein, after each washing step, the portion of the body that is washed is not rinsed.

18. The method of claim 1, wherein all of the cloths in the sealed package are used to wash selected portions of a single body.

19. A method for washing four or more selected portions of a body comprising the steps of:

(a) providing a factory-made sealed package containing four or more cloths, each cloth carrying a cleanser;

(b) removing a cloth from the package and using the removed cloth to wash only one selected portion of the body;

(c) repeating step (b) until each selected portion of the body has been washed; and (d) disposing of each cloth after use.

20. The method of claim 19, wherein the number of selected body portions is at least eight and the package contains at least eight cloths.

21. The method according to claim 19 wherein the selected portions of the body include the head, the neck and chest area, the right arm, the left arm, the right leg, the left leg, the perineum, the back and the buttocks.

22. The method of claim 19, wherein each cloth comprises a blend of natural and synthetic fibers.

23. The method of claim 19, wherein the cleanser comprises a non-ionic surfactant.

24. The method of claim 19, wherein, after each washing step, the portion of the body that is washed is not rinsed.

25. The method of claim 19, wherein all of the cloths in the sealed package are used to wash selected portions of a single body.

26. A method for washing eight or more selected portions of a body comprising:

providing a factory-made sealed package containing at least eight non-woven cloths, each cloth carrying a cleanser;

heating the package and cloths contained therein to a selected temperature, said selected temperature being at least room temperature;

removing each cloth from the package and using each removed cloth to wash only one selected portion of the body; and disposing of each cloth after use; wherein the selected portions of the body include the head, the neck and chest area, the right arm, the left arm, the right leg, the left leg, the perineum, the back and the buttocks, and further wherein after the washing steps the body is not rinsed.

* * * * *